(12) United States Patent
Chang et al.

(10) Patent No.: US 7,959,952 B2
(45) Date of Patent: Jun. 14, 2011

(54) METHOD FOR SKIN CARE

(75) Inventors: Wen-Liang Chang, Taipei (TW);
Tsu-Chung Chang, Taipei (TW);
Hang-Ching Lin, Taipei (TW); Yuan Yang, Taipei (TW)

(73) Assignee: Nuliv Holding Inc., Taipei (TW)

( * ) Notice: Subject to any disclaimer, the term of this patent is extended or adjusted under 35 U.S.C. 154(b) by 46 days.

(21) Appl. No.: 11/469,659

(22) Filed: Sep. 1, 2006

(65) Prior Publication Data

US 2008/0057010 A1    Mar. 6, 2008

(51) Int. Cl.
*A61K 36/00*    (2006.01)
*A61K 36/481*   (2006.01)
*A61K 8/97*     (2006.01)
*A61K 36/48*    (2006.01)

(52) U.S. Cl. ........... 424/725; 424/74; 424/757; 424/773

(58) Field of Classification Search ................ None
See application file for complete search history.

(56) References Cited

U.S. PATENT DOCUMENTS

| 2005/0136140 | A1  | 6/2005  | Chou |   |
|---|---|---|---|---|
| 2007/0154435 | A1* | 7/2007  | Harley | 424/70.13 |
| 2007/0259014 | A1* | 11/2007 | Kim | 424/402 |

FOREIGN PATENT DOCUMENTS

| CN | 1318381       | * | 10/2001 |
| JP | 62012791 A    | * | 1/1987  |
| JP | 03220128 A    | * | 9/1991  |
| JP | 2005194246    | * | 7/2005  |
| KR | 2005073918    | * | 7/2005  |
| WO | 2005/000248 A2 |  | 1/2005  |

OTHER PUBLICATIONS

Ma et al., Chemical analysis of radix Astragali (Huangqi) in China: a comparison with its adulterants and seasonal variations. J Agric Food Chem 50: 4861-4866, 2002.*
Ma et al., Chemical analysis of radix Astragalli (Huangqi) in China: a comparison with its adulterants and seasonal variations. J Agric Food Chem 50: 4861-4866, 2002.*
International Search Report for the corresponding International Patent Application No. PCT/US07/77326; Mailed Apr. 11, 2008; 3 pages.
Viennet, et al., "Effects of astragaloside on growth and apoptosis of fibroblasts from human skin with and without wrinkle in vitro", *Chinese Journal of Medical Aesthetics and Cosmetology*, vol. 12,, No. 2, p. 93-97, 2006.

* cited by examiner

*Primary Examiner* — Qiuwen Mi
(74) *Attorney, Agent, or Firm* — Occhiuti Rohlicek & Tsao LLP (57) ABSTRACT

A method for skin care includes administering the water insoluble fraction of *Astragalus membranaceus*, or astragaloside compounds thereof to a subject in need thereof at an effective amount for improving skin texture, reducing wrinkles, UV protection, and/or providing an anti-aging effect.

6 Claims, 1 Drawing Sheet

FIG. 1

METHOD FOR SKIN CARE

BACKGROUND OF THE INVENTION

The present invention relates to a method for skin care, and particularly to a method for skin care using the water insoluble fraction, organic fraction, or active components of *Astragalus membranaceus*.

Astragalus is derived from the root of a plant, known as *Astragalus membranaceus*. It is also known as milk vetch root (referring to astragalus species that grow in the United States) and Huang-Qi. Astragalus has often been used by practitioners of traditional Chinese medicine to strengthen or tone the body's overall vitality, improve digestion, and support the spleen. Studies confirmed that it contains medicinally active compounds, including a polysaccharide that stimulates the immune system.

Research has also shown that subjects with advanced cancer showed a two to three fold increase in the strength of their immune response after being given astragalus. A second study showed that astragalus boosted immune response, even in animals that were treated with an immunosuppressive drug, cyclophosphamide. Astragalus is taken in China by cancer patients to boost immunity after drug or radiation treatment. It may protect body cells against heavy metals and chemical toxins.

However, none of the studies is directed to an extract from *Astragalus membranaceus* used for skin care.

BRIEF SUMMARY OF THE INVENTION

One aspect of the invention is to provide a method for skin care, which comprises administering the water insoluble fraction of *Astragalus membranaceus* to a subject in need thereof at an effective amount for improving skin texture, reducing wrinkles, ultraviolet (UV) protection, and anti-aging effects. In an example of the invention, the water insoluble fraction of *Astragalus membranaceus* is prepared by a process comprising the steps of extracting *Astragalus membranaceus* with an alcohol to obtain an alcohol extract; and extracting the alcohol extract with water washed to obtain a water insoluble fraction.

In another aspect, the invention provides a method for skin care comprising administering a cycloartane compound of formula (I) to a subject in need thereof at an effective amount for anti-aging effect and UV protection:

Formula (I)

wherein $R_1$ is selected from a group consisting of H, OH, O-acetyl, O-xylopyranosyl, O-(2-acetylxylopyranosyl), O-(3-acetylxylopyranosyl), O-(2,3-diacetylxylopyranosyl), O-(2,4-diacetylxylopyranosyl), O-xylopyranosyl-(1-2)-β-D-glucopyranosyl, O-xylopyranosyl-(1-2)-α-arabinopyranosyl, $R_2$ is selected from a group consisting of H, OH, O-acetyl, O-glucopyranosyl, O-xylopyranosyl, $R_3$ is selected from a group consisting of H, OH and O-acetyl, and $R_4$ is selected from a group consisting of Additional features and advantages of the present invention will be set forth in part in the description which follows, and in part will be obvious from the description, or may be learned by practice of the invention. The features and advantages of the invention will be realized and attained by means of the elements and combinations as described.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings.

In the drawings.

DETAILED DESCRIPTION OF THE INVENTION

Reference will now be made in detail to the present embodiments of the invention. For a better understanding of the present invention, some of the terms used herein are explained in more detail.

As used herein, the article "a" or "an" means one or more than one (that is, at least one) of the grammatical object of the article, unless otherwise made clear in the specific use of the article in only a singular sense.

An "effective amount" as used herein refers to an amount that provides anti-aging effect, ultraviolet (UV) protection or both in a subject in need thereof. For those skilled in the art, the effective amount, as well as dosage and frequency of administration, may easily be determined according to their knowledge and standard methodology of merely routine experimentation based on the present disclosure.

The present invention provides a method for skin care, which comprises administering a water insoluble fraction of *Astragalus membranaceus* to a subject in need thereof at an effective amount for improving skin texture, reducing wrinkles, UV protection and anti-aging effect. In an example of the invention, the water insoluble fraction of *Astragalus membranaceus* is prepared by a process comprising the steps of extracting *Astragalus membranaceus* with an alcohol to obtain an alcohol extract; and extracting the alcohol extract with water to obtain a water insoluble fraction.

In accordance with one embodiment, the water insoluble fraction of *Astragalus membranaceus* comprises astragaloside of the formula (I):

Formula (I)

wherein $R_1$ is selected from a group consisting of H, OH, O-acetyl, O-xylopyranosyl, O-(2-acetylxylopyranosyl), O-(3-acetylxylopyranosyl), O-(2,3-diacetylxylopyranosyl), O-(2,4-diacetylxylopyranosyl), O-xylopyranosyl-(1-2)-β-D-glucopyranosyl, O-xylopyranosyl-(1-2)-α-arabinopyranosyl, $R_2$ is selected from a group consisting of H, OH, O-acetyl, O-glucopyranosyl, O-xylopyranosyl, $R_3$ is selected from a group consisting of H, OH and O-acetyl, and $R_4$ is selected from a group consisting of.

In a example of the invention, the water insoluble fraction comprises astragaloside of the formula (II):

Formula (II)

wherein $R_A$, $R_B$, $R_C$, and $R_D$ are selected from a group consisting of acetyl (Ac), hydrogen (H) and glucopyranoside (Glc).

In a preferable embodiment of the invention, the water insoluble fraction of *Astragalus membranaceus* comprises astragaloside of the formula (II), wherein $R_A$ is Ac, $R_B$ is Ac, $R_C$ is H and $R_D$ is Glc; for example, astragaloside I.

In accordance with another preferable embodiment of the invention, the water insoluble fraction of *Astragalus membranaceus* comprises astragaloside of the formula (II), wherein $R_A$ is Ac, $R_B$ is H, $R_C$ is H and $R_D$ is Glc; for example, astragaloside II.

In accordance with a preferable embodiment of the invention, the water insoluble fraction of *Astragalus membranaceus* comprises astragaloside of the formula (II), wherein $R_A$ is Glc, $R_B$ is H, $R_C$ is H and $R_D$ is H; for example, astragaloside III.

In accordance with a preferable embodiment of the invention, the water insoluble fraction of *Astragalus membranaceus* comprises astragaloside of the formula (II), wherein $R_A$ is H, $R_B$ is H, $R_C$ is H and $R_D$ is Glc; for example, astragaloside IV.

In accordance with one preferable embodiment of the invention, the water insoluble fraction of *Astragalus membranaceus* comprises astragaloside of the formula (II), wherein $R_A$ is Glc, $R_B$ is H, $R_C$ is H and $R_D$ is Glc; for example, astragaloside VI.

In accordance with a preferable embodiment of the invention, the water insoluble fraction of *Astragalus membranaceus* comprises astragaloside of the formula (II), wherein $R_A$ is Ac, $R_B$ is H, $R_C$ is Ac and $R_D$ is Glc; isoastragaloside I.

In accordance with a preferable embodiment of the invention, the water insoluble fraction of *Astragalus membranaceus* comprises astragaloside of the formula (II), wherein $R_A$ is H, $R_B$ is Ac, $R_C$ is H and $R_D$ is Glc; isoastragaloside II.

In another example of the invention, the water insoluble fraction of *Astragalus membranaceus* comprises astragaloside of formula (I), wherein $R_1$ is OH, $R_2$ is O-glucopyranosyl, $R_3$ is OH, and $R_4$ is

For example, the water insoluble fraction comprises cylcoastragenol-6-O-β-D-glucopyranoside.

As the results of the experiments performed in the invention, the water insoluble fraction was administered to enhance cellular expression and secretion of collagens I and III, promote glucosamine and proline uptakes, up-regulate the hyaluronic acid (HA) expression, and down-regulate the expression and proteolytic activity of matrix metalloproteinases (MMPs). In an embodiment of the invention, the cells were treated with a dosage of about 0.25-40 μg/mL of the water insoluble fraction to obtain a good performance as described above.

In addition, the invention provides a method for skin care comprising administering an astragaloside compound of formula (I) to a subject in need thereof at an effective amount for providing anti-aging effect and UV protection. The definitions of the substituents are defined as above.

In an embodiment of the invention, the astragaloside compound comprises astragaloside of the formula (II), the definitions of the substituents and the preferable embodiments are given above.

In an embodiment of the invention, the astragaloside compound comprises astragaloside of formula (I), wherein $R_1$ is OH, $R_2$ is O-glucopyranosyl, $R_3$ is OH, and $R_4$ is for example, cylcoastragenol-6-O-β-D-glucopyranoside.

Similarly, as the results of the experiments conducted in the invention, the cellular expression of collagens I and III was enhanced, glucosamine and proline uptakes were promoted, HA expression was up-regulated, and the expression and proteolytic activity of MMP were down-regulated when an astragaloside compound according to the invention was administered, at such as a dosage of about 0.01-10 μM. The enhanced MMP expression triggered by UV irradiation was also suppressed, suggesting that this compound protect collagen from degradation elicited by MMP. The astragalosides of formulae (I) and (II) and the water insoluble fraction can serve as agents for the prevention and treatment of skin aging and UV protection for the skin.

In another embodiment of the invention, when the cosmetic cream comprising the water insoluble fraction of *Astragalus membranaceus* was applied on test subjects' skin, the facial skin of the test subjects looked more radiant and whitening as indicated by parameters for measuring the erythema and melanin. Also, the pH of the facial skin was reduced to a level, which prevented growth of the microorganism. Furthermore, the wrinkle area on the test subjects' face was significantly reduced.

The water insoluble fraction of *Astragalus membranaceus* may be obtained by any standard or known methods or technologies well known to or commonly used by those skilled in the art. For instance, the water insoluble fraction of *Astragalus membranaceus* may be obtained by the steps of providing *Astragalus membranaceus*, preferably in a powder form, extracting it with alcohol to obtain an alcohol extract, and further extracting the alcohol extract with water to take a water insoluble fraction. In one preferred embodiment, the alcohol extract is extracted with an alcohol (such as 95% alcohol) to obtain an alcohol fraction. However, it should be noted that the alcohol extract is not limited to the water insoluble fraction and alcohol fraction of *Astragalus membranaceus* described above.

The present invention also provides a cosmetic cream comprising the water insoluble fraction of *Astragalus membranaceus*, or an astragaloside compound according to the invention. And the cosmetic cream may be formulated with other ingredients for making the basic cream. For example, the ingredients include but are not limited to Water, Isononyl Isononanoate, Butylene Glycol, Triethylhexanoin, Behenyl Alcohol, PEG-100 Hydrogenated Castor Oil, Glyceryl Stearate SE, Dimethicone, Macadamia Nut Oil, Jojoba Oil, Hydrogenated Lecithin, Methylparaben, DL-α-Tocopheryl Acetate, Butylparaben, Phenoxyethanol and Fragrance.

It is noted that the present invention is not limited to only applications in cosmetics, other pharmaceutical applications, such as treatments in diseases associated with a deficiency in collagen I, collagen III, glucosamine, proline or hyaluronic acid (HA) and an increased expression or activation of matrix metalloproteinases (MMPs) in the patients may also be encompassed by the scope of the invention.

The present invention is more specifically explained by the following examples. However, it should be noted that the present invention is not limited to these examples in any manner.

EXAMPLE 1

Preparation of the Water Insoluble Fraction of *Astragalus Membranaceus*

Powdered of the roots of *Astragalus membranaceus* (1.0 kg), from Formosa Kingstone Bioproduct International Co. Ltd., were extracted with 95% alcohol (×3) at 50° C. for 2 hr. The combined extract was concentrated in vacuo to yield an alcohol extract about 127.8 g. The alcohol extract (127.8 g) was washed with distilled water for 3 times to yield a water-insoluble fraction (33.9 g) and a water-soluble fraction (93.9 g).—The alcohol extract (100.0 g) was dissolved in distilled water and partitioned (1:1) with n-butanol, and then a butanol fraction (63.0 g) was obtained.

EXAMPLE 2

Effects of the Water Insoluble Fraction of *Astragalus Membranaceus* and Astragalosides on Collagen Expression in Human HaCaT Cells and Human HDF Cells HaCaT Cell Culture The Spontaneously transformed human keratinocyte cell lines HaCaT cells were grown at 37° C. in a humidified incubator under 5% $CO_2$ and 95% air in culture medium such as Dulbecco Modified Eagle Medium (DMEM) supplemented with 10% Fetal Bovine Serum (FBS), 100 IU/mL penicillin, 100 μg/mL of streptomycin, 2 mM sodium pyruvate and 1% Non-Essential Amino Acids (NEAA). The culture medium was replaced every other day. After confluence, the cells were subcultured following trypsinization. For subcultures cells were harvested after brief treatment with 0.1% trypsin/ethylenediaminetetraacetic acid (EDTA) solution and seeded at a dilution of 1:10. Cells between passages 12 and 45 were used for studies. The cells were seeded and incubated for 24 h before treated with the astragalosides for 24 h. Control cultures were maintained in medium supplemented with vehicle (dimethyl sulfoxide (DMSO) 0.1%). No growth and differentiation effects of DMSO were observed under these culture conditions.

HDF Cell Culture

Primary human dermal fibroblasts cells (HDF) were purchased from Cascade Biologics (Portland, Oreg., USA) and cultured in medium 106 supplemented with 10% fetal bovine serum (FBS), 100 IU/mL penicillin, 100 μg/mL of streptomycin. The cells from passages 4 to 10 were used for this study. Culture medium was replaced every other day. After confluence, the cells were subcultured following trypsinization. For subcultures cells were harvested after brief treatment with 0.1% trypsin/EDTA solution and seeded at a dilution of 1:10. The cells were seeded at $1 \times 10^5$ cells in 6-well culture plate for 24 h before treated with astragalosides or crude extracts, such as butanol fraction and water insoluble fraction of *Astragalus membranaceus* for the indicated time periods. Control cultures were maintained in medium supplemented with vehicle (dimethyl sulfoxide, DMSO, 0.1%). No growth and differentiation effects of DMSO were observed under these culture conditions.

Astragaloside Treatment

The cells were treated with pure compounds such as astragaloside I (AS1), astragaloside II (AS2), astragaloside III (AS3), astragaloside IV (AS4), astragaloside VI (AS6), isoastragaloside I (isoAS1), isoastragaloside II (isoAS2), and cycloastragenol 6-O-β-D-glucopyranose (AA) at concentrations of 0-10 μM. Alternatively, the cells were also treated with the crude extracts, such as butanol fraction and water insoluble fraction of *Astragalus membranaceus* at concentrations of 0, 1, 10, and 40 μg/mL. The cells were treated with the indicated compounds or the extracts for 24 h before harvested for analysis of collagen I and III expressed in the whole cell extract or secreted into the culture medium.

Western Blot

Western blot analysis was carried out on both of cultured medium and cell lysates. The cells were plated on 6-cm dishes at a density of $1 \times 10^6$ cells/dish for 24 h prior to treatment with indicated concentrations of *astragalus* triterpenoids as indicated for another 48 h. The conditioned culture mediums were then centrifuged, 2-fold concentrated and collected for assay of collagens and MMPs secreted into the culture medium. The cells were washed and lysed in 0.2 mL of lysis buffer (1% NP-40, 50 mM Tris-HCl, pH 7.4, 180 mM NaCl, 1 mM EDTA, 1 mM PMSF, 1 mM NaF, 10 mM $Na_3VO_4$) for 30 min at 4° C. After centrifuging at 17500 g for 15 min, the supernatants of cell lysate were also collected. Protein concentration of the samples were measured using the bicinchoninic acid (BCA) protein assay kit according to the manufacturer's protocol (Pierce, Rockford, Ill., USA). Equal amount of protein samples of concentrated conditioned medium (100 μg) or cell lysate supernatants (50 μg) were mixed with an appropriate volume of 4×SDS sampling buffer and separated by 8% SDS-PAGE gel. The protein bands separated in the SDS-PAGE gel were blotted onto a polyvinylidene fluoride (PVDF) membrane. The blotted PVDF membrane was washed twice and blocked in freshly prepared Tris-buffered saline (TBS) containing 0.1% Tween-20 and 7% skim milk (TBST) for 2 h at room temperature. The PVDF membrane was then incubated with either antibodies against collagen I and III or the housekeeping protein α-tubulin (Santa Cruz Biotechnology, Santa Cruz, Calif.) for 18 h at 4° C. Horseradish peroxidase-conjugated anti-goat antibody was used as secondary antibody. Signals were visualized by an enhanced chemiluminescence kit (Clonetech, Palo Alto, Calif., USA) followed by exposure to X-ray films.

Results shown represent the quantitated data from western blot analysis. Generally, as shown in Table 1A, the collagen I was over-expressed in the human HaCaT cells treated with different dosages (0.01, 0.1 and 1 μM) of the astragalosides, such as AS1, AS2, isoAS1, isoAS2 and AA. The collagen I was also over-expressed in the human HaCaT cells treated with 40 μg/mL of astragaloside extract.

TABLE 1A

| | Collagen I in cell | | | |
|---|---|---|---|---|
| compound (in μM) | 0 | 0.01 | 0.1 | 1 |
| AS1 | 1.00 | 1.13 | 0.72 | 1.22 |
| AS2 | 1.00 | 0.86 | 1.14 | 1.87 |
| isoAS1 | 1.00 | 1.13 | 1.06 | 1.19 |
| isoAS2 | 1.00 | 1.52 | 0.94 | 1.41 |
| AA | 1.00 | 2.57 | 3.34 | 3.47 |

| | Collagen 1 in cell | | | |
|---|---|---|---|---|
| compound (in μg/mL) | 0 | 1 | 10 | 40 |
| water insoluble fraction | 1.00 | 1.00 | 0.95 | 1.13 |

The collagen III was also over-expressed in the human HaCaT cells treated with different doses (0.01, 0.1 and 1 μM) of the astragalosides, such as AS1, AS2 and AS3. Similarly, the collagen III was over-expressed in the human HaCaT cells treated with various dosages (1, 10 and 40 μg/mL) of the crude extract as shown in Table 1B. On the other hand, the amount of collagen III secreted into the medium was measured to determine the effect on cellular release of collagen III. In table 1B, the collagen III was over-expressed in the cell medium when the human HaCaT cells were treated with different dosages (0.01, 0.1 and 1 μM) of the astragalosides, such as AS4, AS6 and isoAS1.

TABLE 1B

| | Collagen III in cell | | | |
|---|---|---|---|---|
| compound (in μM) | 0 | 0.01 | 0.1 | 1 |
| AS1 | 1.00 | 1.29 | 1.59 | 2.63 |
| AS2 | 1.00 | 1.36 | 1.44 | 1.49 |
| AS3 | 1.00 | 0.86 | 1.22 | 2.12 |

| | Collagen III in cell | | | |
|---|---|---|---|---|
| compound (in μg/mL) | 0 | 1 | 10 | 40 |
| water insoluble fraction | 1.00 | 1.28 | 2.66 | 1.88 |

| | Collagen III in medium | | | |
|---|---|---|---|---|
| compound (in μM) | 0 | 0.01 | 0.1 | 1 |
| AS4 | 1.00 | 0.79 | 1.13 | 1.16 |
| AS6 | 1.00 | 4.55 | 4.27 | 3.86 |
| isoAS1 | 1.00 | 3.32 | 4.41 | 6.53 |

The collagen expression in the human HDF cells was also determined. According to the results listed in Table 2A, it was found that collagen I was over-expressed in the human HDF cells treated with the astragalosides including AS2, AS4, AS6, isoAS1 and AA. And Collage I was over-expressed in the cells treated with various doses (1, 10, 40 μg/mL) of the crude extracts, such as butanol fraction and water insoluble fraction of *Astragalus membranaceus*. In addition, the expression of collagen I was also observed in the culture medium, suggesting that an increased amount of the collagen I was secreted into the medium when the cells were treated with either the astragalosides or the crude extract.

TABLE 2A

| compound | Collagen I in cell | | | | Collagen I in medium | | | |
|---|---|---|---|---|---|---|---|---|
| (in μM) | 0 | 0.01 | 0.1 | 1 | 0 | 0.01 | 0.1 | 1 |
| AS2 | 1.00 | 1.02 | 0.73 | 1.26 | 1.00 | 1.24 | 1.15 | 1.02 |
| AS4 | 1.00 | 1.16 | 1.33 | 1.07 | 1.00 | 1.24 | 1.11 | 1.11 |
| AS6 | 1.00 | 1.18 | 1.41 | 1.30 | 1.00 | 1.19 | 1.29 | 1.25 |
| isoAS1 | 1.00 | 0.71 | 1.11 | 1.27 | 1.00 | 1.20 | 1.08 | 0.96 |
| AA | 1.00 | 1.04 | 1.85 | 1.17 | 1.00 | 0.97 | 0.95 | 1.52 |

| compound | Collagen I in cell | | | | Collagen I in medium | | | |
|---|---|---|---|---|---|---|---|---|
| (in μg/mL) | 0 | 1 | 10 | 40 | 0 | 1 | 10 | 40 |
| butanol fraction | 1.00 | 1.88 | 1.62 | 2.29 | 1.00 | 1.12 | 1.08 | 1.20 |
| water insoluble fraction | 1.00 | 0.95 | 0.99 | 1.63 | 1.00 | 1.28 | 1.40 | 1.72 |

Moreover, as shown in Table 2B below, the expression of collagen III was also observed both in the cell and in the culture medium when the human HDF cells were treated with different doses of the crude extracts. Therefore, the results from the western blotting analysis generally suggest overexpression of the collagen I and collagen III in human HaCaT and HDF cells and their increased release into the culture medium.

TABLE 2B

| | Collagen III in cell | | | |
|---|---|---|---|---|
| compound (in μM) | 0 | 0.01 | 0.1 | 1 |
| AS1 | 1.00 | 1.16 | 1.08 | 1.18 |
| AS6 | 1.00 | 1.65 | 1.37 | 0.95 |
| compound (in μg/mL) | 0 | 1 | 10 | 40 |
| butanol fraction | 1.00 | 0.69 | 1.45 | 2.75 |
| water insoluble fraction | 1.00 | 2.71 | 3.10 | 1.81 |
| | Collagen III in medium | | | |
| compound (in μM) | 0 | 0.01 | 0.1 | 1 |
| AS1 | 1.00 | 1.38 | 1.19 | 1.77 |
| AS2 | 1.00 | 1.26 | 1.74 | 0.94 |
| AS3 | 1.00 | 2.18 | 1.79 | 1.51 |
| isoAS2 | 1.00 | 1.00 | 1.07 | 1.18 |
| AA | 1.00 | 1.03 | 1.62 | 1.34 |
| compound (in μg/mL) | 0 | 1 | 10 | 40 |
| water insoluble fraction | 1.00 | 1.55 | 2.32 | 2.83 |

EXAMPLE 3

Effect of Astragalosides on Proline Uptake in Human HaCaT Cells

Proline Uptake Assay

The proline uptake assay was carried out as described (*Biochim Biophys Acta.* 1104:283-292, 1992). Briefly, HaCaT cells were seeded into a 24-well plate at a density of $3 \times 10^4$ cells/well and cultured for 24 h. The cells were then treated in the absence (solvent control) or presence of various concentrations of astragalosides or crude extracts from *Astragalus membranaceus* for another 48 h. The treated cells were then washed once with PBS and incubated in amino acid free medium (AAFM) for another 30 min. The treated cells were them replaced with fresh AAFM containing 50 μg/ml of ascorbate and total of 0.5 mM of L-proline containing 1 μCi [$^3$H] Proline (American Radiolabelled Chemicals Inc, ARC, St. Louis, Mo., USA). At designated time interval, the cells were washed with AAFM containing cold proline and then lysed in 200 μL of 2% SDS. Cell lysates were centrifuged at 15000 g for 15 min. Intracellular proline uptaken by the cells was determined by transferring 10 μL of the cell lysate to filter-bottomed UniFilter plates (Perkim-Elmer) and counted. Protein concentration of the samples were measured using the BCA protein assay kit as described above. Proline accumulated in the cells was calculated and normalized to protein concentration and uptake rate was expressed as nmole of L-proline per minute per milligram of cell protein (nmole/min/μg).

TABLE 3

| | Uptake rate(pMol/mg/min) | Percentage (%) |
|---|---|---|
| Control | 0.6904 ± 0.0225 | 100.00 |
| 0.1 μM AS1 | 0.8627 ± 0.0741 | 124.97 |
| 0.1 μM AS2 | 0.9770 ± 0.1119 | 141.52 |

TABLE 3-continued

| | Uptake rate(pMol/mg/min) | Percentage (%) |
|---|---|---|
| 0.1 μM AS3 | 0.7213 ± 0.0090 | 104.48 |
| 0.1 μM AS4 | 0.7628 ± 0.1015 | 110.50 |
| 2.5 μg/mL water insoluble fraction | 0.7196 ± 0.0308 | 103.68 |
| 0.25 μg/mL butanol fraction | 0.7288 ± 0.0401 | 105.56 |
| 0.50 μg/mL butanol fraction | 0.8230 ± 0.0573 | 119.20 |
| 1 μg/mL butanol fraction | 0.7499 ± 0.0577 | 108.62 |

From the results listed in Table 3, it was found that the crude extract has enhanced the proline uptake by 124.97%, 119.2% and 108.62% in human HaCaT cells as compared to the control group, suggesting that the crude extract had a promoting effect on the cellular uptake of proline.

EXAMPLE 4

Effect of Astragalosides on Hyaluronic Acid (HA) Expression in Human HaCaT Cells HA Measurement HA measurement was carried out as described (*BBRC*, 2004, 316: 348-355). Briefly, HaCaT or HDF cells were seeded and incubated in 24-well plates to confluency. Immediately before experiments, cells were washed twice with serum-free medium to completely remove HA accumulated during cell growth. The cells were then cultured with or without different compounds in 0.5 ml serum-free medium for 48 h. At the indicated time, aliquots of medium were removed, centrifuged at 15000 g for 5 min, and supernatants were analyzed for HA using an enzyme-linked immunosorbent assay (ELISA) kit (Echelon Bioscience, Salt Lake, Utah).

Results shown represent the fold of induction of the astragalosides on hyaluronic acid expression in HaCaT cells. The concentrations of astragalosides used were 0, 1, or 10 μM (unless indicated otherwise) for astragaloside pure compounds; were 0, 0.5, 1, 2.5, 5, 10, 40 μg/mL for the butanol fraction (unless indicated otherwise); and were 0, 1, 10, 40 μg/mL for the water insoluble fraction (unless indicated otherwise). The cells were treated with the indicated compounds for 24 h before harvested for analysis of secreted hyaluronic acid in culture medium using HA-ELISA kit.

The cells treated with 1 μM or 10 μM of the astragalosides AS1, AS2, AS4 and AS6 have all shown increased cellular secretion of HA as evident in the increased HA expression in the medium. And in the human HaCaT cells, the crude extracts of different doses (1, 10 and 40 μg/mL) have also promoted the cellular secretion of HA into the medium as shown in Table 4A.

TABLE 4A

| | HA in medium | | |
|---|---|---|---|
| compound (in μM) | 0 | 1 | 10 |
| AS1 | 1.00 | 1.45 | 1.36 |
| AS2 | 1.00 | 1.98 | 1.31 |
| AS4 | 1.00 | 2.27 | 1.31 |
| AS6 | 1.00 | 1.13 | 1.38 |

TABLE 4A-continued

| | HA in medium | | | | | | |
|---|---|---|---|---|---|---|---|
| compound (in µg/mL) | 0 | 0.5 | 1 | 2.5 | 5 | 10 | 40 |
| butanol fraction | 1.00 | 0.98 | 1.02 | 1.02 | 0.98 | 1.03 | 1.33 |
| compound (in µg/mL) | 0 | | 1 | | 10 | | 40 |
| water insoluble fraction | 1.00 | | 1.16 | | 1.20 | | 1.19 |

Quantitative Analyses of the HA Synthase 2 (HAS2) Transcripts

Relative levels of HAS2 expression in HaCaT cells were determined by real-time quantitative reverse transcriptase polymerase chain reaction (qRT-PCR). Total RNAs were isolated from the cultured human cells using TRIzol reagent (Invitrogen, Irvine, Calif., USA). 1 µg of RNA was reverse transcribed, at 37° C. for 60 min in a 20 µl transcription mixture containing dNTP (0.5 mM), oligo-dT (0.1 µg), RNasin (10 units), 1×PCR buffer (20 mM Tris-HCl, pH 8.3; 2.5 mM $MgCl_2$; 50 mM KCl), and 100 units of Moloney murine leukemia virus reverse transcriptase (Invitrogen). The cDNA product was phenol extracted, ethanol precipitated, and resuspended in 20 µl TE (20 mM Tris-Cl, pH 8.0 and 1 mM EDTA). qRT-PCR was performed using the Applied Biosystem 7300 system and pre-developed Taqman Gene Expression Assays (Applied Biosystems, Foster City, Calif., USA). The reaction mixtures (20-µl total volume) contained 2 µl of serially diluted cDNA, 10 µl of Taqman Universal PCR Master Mix (Applied Biosystems), and 1 µl of either human HAS-2 gene (assay ID Hs 00193435_ml, Applied Biosystems), or GAPDH primer mix (assay ID Hs99999905_ml, Applied Biosystems). The reactions were amplified as follows: 50° C. for 2 min and 95° C. for 10 min, followed by 40 cycles of 95° C. for 1 min and 65° C. for 1 min. Two independent triplicate experiments were performed for the selected genes. Relative quantitation was performed using the 7300 software (Applied Biosystems, Foster City, Calif., USA). Expression of HAS-2 was normalized to GAPDH expression in each sample.

As evident in table 4B, HAS-2 was over-expressed in the human HaCaT cells regardless of whether the cells were treated with 0.1 µM of the astragalosides, such as AS2, AS4, isoAS1 or isoAS2 or treated with 2.5 µg/mL, 5.0 µg/mL of the butanol fraction of *Astragalus membranaceus* or 40 µg/mL of the water insoluble fraction of *Astragalus membranaceus*. Therefore, the results in tables 4A and 4B suggest that the astragalosides or the crude extracts had a promoting effect on the HA expression in the human HaCaT cells.

TABLE 4B

| | HAS-2 in cell | |
|---|---|---|
| compound (in µM) | 0 | 0.1 |
| AS2 | 1.00 | 2.73 |
| AS4 | 1.00 | 1.41 |
| isoAS1 | 1.00 | 1.12 |
| isoAS2 | 1.00 | 1.28 |

TABLE 4B-continued

| | HAS-2 in cell | | | |
|---|---|---|---|---|
| compound (in µg/mL) | 0 | 1.0 | 2.5 | 5.0 |
| butanol fraction | 1.0 | 0.81 | 1.40 | 1.89 |
| compound (in µg/mL) | 0 | 1 | 10 | 40 |
| water insoluble fraction | 1.00 | 0.90 | 0.92 | 3.63 |

EXAMPLE 5

Effect of Astragalosides on Glucosamine Uptake in Human HaCaT Cells

Glucosamine Uptake Assay

Glucosamine is the primary building block of HA. Therefore, a measurement of glucosamine uptake by the cells suggests synthesis of HA in human cells.

In glucosamine uptake test, HaCaT cells were seeded into 24-well plate at a density of $3 \times 10^4$ cells/well and cultured for 24 h. The cells were then treated in the absence (solvent control) or presence of various concentrations of astragalosides for another 48 h. The treated cells were then washed twice with PBS and incubated in glucose and serum free medium (GSFM). After 2 h, the cells were replaced with fresh GSFM containing 0.2 µCi of [$^{14}$C]-Glucosamine (American Radiolabelled Chemicals Inc, ARC, St. Louis, Mo., USA). At the designated time interval, the cells were washed twice with GSFM containing cold glucosamine and then lysed in 200 µL 2% SDS. Cell lysates were centrifuged at 15000 g for 15 min. Intracellular uptaken glucosamine was determined by transferring 10 µL of the cell lysate to filter-bottomed UniFilter plates (Perkim-Elmer) and counted. Protein concentration of the samples was measured using the BCA protein assay kit as described above. Glucosamine accumulated in the cells was calculated and normalized to protein concentration and uptake rate was expressed as counts per minute per microgram of cell protein (cpm/min/µg).

As shown in Table 5, the glucosamine uptake rate increased when the cells were treated with 0.1 µM of the astragalosides AS1, AS2, AS3, IsoAS1 and IsoAS2, indicating promoting effect of the astragaloside on the glucosamine uptake.

TABLE 5

| | Uptake rate(CPM/µg protein) | Percentage (%) |
|---|---|---|
| Control | 0.8242 ± 0.0321 | |
| 0.1 µM AS1 | 1.0482 ± 0.0560 | 127.18 |
| 0.1 µM AS2 | 0.9561 ± 0.0918 | 116.00 |
| 0.1 µM AS3 | 1.0129 ± 0.0371 | 122.90 |
| 0.1 µM AS4 | 0.8931 ± 0.0918 | 108.36 |
| 0.1 µM AS6 | 0.8471 ± 0.0278 | 102.78 |
| 0.1 µM AA | 0.9445 ± 0.0823 | 114.59 |
| 0.1 µM IsoAS1 | 0.9589 ± 0.0665 | 116.34 |
| 0.1 µM IsoAS2 | 0.9226 ± 0.0668 | 111.94 |

EXAMPLE 6

Effect of Astragalosides on Matrix Metalloproteinase (MMPs) Expression in Human HaCaT-1 and HDF-1 Cells Matrix metalloproteinase-1 (MMP-1) is an enzyme that digests interstitial collagens and other extracellular matrix macromolecules. Matrix metalloproteinase-1 is the primary collagenase Therefore, a presence of the MMP-1 or its proteolytic activity would indicate that the collagen is down-regulated. On the other hand, a reduced activity or expression of the MMP-1 would suggest that the collagen may be abundant in the cells.

UV Irradiation

To characterize the effects of astragalosides on the expression level of MMPs in human cells, HDF or HaCaT cells were first treated with or without various concentrations of astragalosides for 24 h. The cells were washed with phosphate-buffered saline (PBS) and irradiated with 10-100 mJ/cm$^2$ of UV-B (312 nm) for HDF-1 and HaCaT cells, respectively, using the UV light irradiator (UVItec unlimited, Cambridge, England). The cells were then washed and incubated with serum free medium for 24 h before harvested for analysis. The effect of astragalosides on MMPs levels was analyzed by western blot and the activity of MMPs was analyzed by zymography. All trans retinoic acid (atRA) was used as a positive control to suppress the UV-B-induced MMPs activation and expression.

Figure 1:
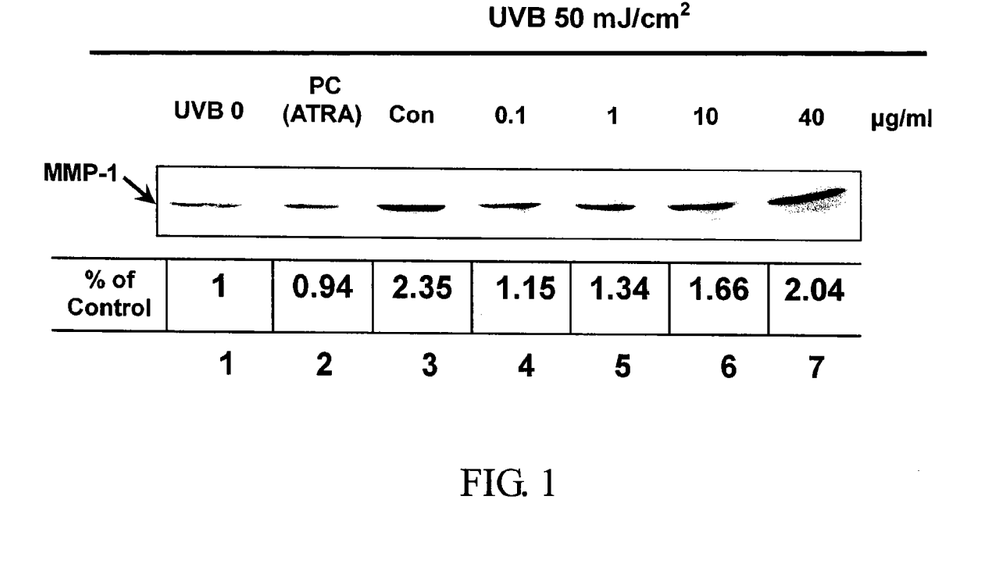
FIG. 1 is a SDS-PAGE gel image showing suppression of MMP-1 expression in human HDF cells treated with astragalosides.

Human HDF cells were treated with the indicated concentrations of water insoluble fraction of *Astragalus membranaceus* for 24 h. The cells were then irradiated with 50 mJ/cm$^2$ of UV-B. After 24 h, the cells were harvested for western blot analysis. As shown in FIG. 1, a basal level of MMP-1 was expressed in cells not irradiated with UV (lane 1, control), UV irradiation induced MMP-1 expression in HDF cells (lane 2), all-trans $R_A$ (atRA) blocked the UV-mediated induction of MMP-1 expression (lane 3, positive control), and the UV-induced MMP-1 expressions were inhibited in cells pretreated with 0.01, 1, 10, and 40 mM of water insoluble fraction of *Astragalus membranaceus* (lane 4 to 7). The results demonstrated that the water insoluble fraction of *Astragalus membranaceus* was efficient in blocking MMP-1 expression triggered by UV irradiation, which suggested that this compound could protect collagen I from degradation elicited by MMP-1. Thus, the water insoluble fraction of *Astragalus membranaceus* is a potential agent for the prevention and treatment of skin aging as a result of UV irradiation.

Zymography

The proteolytic activities of MMPs from HaCaT and HDF cells were measured essentially as described elsewhere (*Circ Res*, 1999; 85:906-911). The cells were seeded for 24 h and then treated with various concentrations of astragalosides for another 48 h. The conditioned culture medium was then centrifuged, 2-fold concentrated, and saved for assay of collagens and MMPs expressed into the culture medium. The cells were then lysed in lysis buffer (1% Triton, 50 mM Tris-Cl, pH 7.4, 180 mM NaCl, 1 mM EDTA). Protein concentration of the samples was measured using the bicinchoninic acid (BCA) protein assay kit as described. Samples of concentrated conditioned medium and cell lysates were mixed with non-reducing electrophoresis loading buffer and subjected to electrophoresis under non-reducing conditions, which was carried out on a 10% SDS-PAGE co-polymerized with 2 mg/mL gelatin or casein (Sigma, St. Louis, Mo. USA). For zymographic analysis of pro-MMP-2 and activated MMP-2, the total 20 µg of culture medium were used for electrophoresis. Following electrophoresis, renaturation of the proteins was achieved by incubating the gels in 25 g/L Triton X-100 at room temperature for 2×10 min. Subsequently the gels were incubated in 50 mM Tris-HCl, pH 7.5 containing 0.2 M NaCl, 0.02% Brij35 and 10 mM CaCl$_2$ at 37° C. for 18 h. After staining the gels with Coomassie Brilliant Blue R-250 and destaining, zones of proteolytic activities became visible as transparent bands in the stained gel. In order to obtain higher sensitivity, the gels were further destained in a solution of 1% Triton x-100 (1 to 2 h). This procedure increased the signal-to-noise ratio, allowing the visualization of faint gelatinase bands at 92, 125 and greater than 200 kDa. Zymograms were read using a Molecular Dynamics (Sunnyvale, Calif., USA) computing laser densitometer with Image Quant software.

Quantitative Analyses of the MMP-1 Transcripts

Relative levels of MMP-1 expression in HDF cells were determined by qRT-PCR. Preparation of total RNA and cDNA were carried out as described in previous sections. qRT-PCR was performed using the Applied Biosystem 7300 system and pre-developed Taqman Gene Expression Assays (Applied Biosystems, Foster City, Calif., USA). The reaction was performed as described in previous sections except that primer mix for human MMP-1 (assay ID HS00233958_ml, Applied Biosystems) and GAPDH (assay ID Hs99999905_ml, Applied Biosystems) were used.

Results shown in Tables 6A and 6B represent the quantitated data from zymography analysis of MMP-2 protein in HaCaT cells and qRT-PCR for MMP-1 in HDF cells. The concentrations used were 0, 0.01. 0.1, 1 µM (if not indicated otherwise) for pure compounds; and were 0, 1, 10, 40 µg/mL for crude extract (if not indicated otherwise). The cells were treated with the indicated compounds for 24 h before harvested for analysis of Pro-MMP-2 or activated MMP-2 in whole cell extract. Fifty micrograms of the cell extract samples were used for electrophoresis.

In accordance with the results in Table 6A, the proteolytic activity of the MMP-2 in the conditioned medium was reduced or weakened when the cells were treated with various doses (0.01, 0.1 and 1 µM) of the astragalosides AS1, AS2, AS3 and AS6, suggesting the collagen was abundant in the human HaCaT cells.

TABLE 6A

| | ProMMP-2/MMP2 in medium | | | |
|---|---|---|---|---|
| compound (in µM) | 0 | 0.01 | 0.1 | 1 |
| AS1 | 1.00 | 0.57 | 0.57 | 0.86 |
| AS2 | 1.00 | 0.89 | 0.89 | 0.67 |
| AS3 | 1.00 | 0.76 | 0.57 | 0.81 |
| AS6 | 1.00 | 0.89 | 0.67 | 0.74 |

The expression of MMP-1 mRNA was reduced in the HDF cells treated with 0.1 µM of the astragalosides AS1, AS2, isoAS1, isoAS2 and AA as shown in Table 6B. In addition, the expression of MMP-1 mRNA decreased when the cells were treated with various doses (1 and 10 µg/mL) of the crude extracts. Therefore, the results from the tables 6A and 6B both suggest that an effective amount of the astragalosides or crude extracts would reduce the expression of MMP-1 and suppress collagen degradation elicited by this enzyme.

TABLE 6B

| | MMP-1 Q-PCR | |
|---|---|---|
| compound (in µM) | 0 | 0.1 |
| AS1 | 1.00 | 0.75 |
| AS2 | 1.00 | 0.25 |
| isoAS1 | 1.00 | 0.6 |
| isoAS2 | 1.00 | 0.71 |
| AA | 1.00 | 0.76 |

TABLE 6B-continued

| | MMP-1 Q-PCR | | | |
|---|---|---|---|---|
| compound (in μg/mL) | 0 | 1.0 | 2.5 | 5.0 |
| butanol fraction | 1.0 | 0.64 | 0.77 | 0.67 |
| compound (in μg/mL) | 0 | | 1 | 10 |
| water insoluble fraction | 1.00 | | 0.44 | 0.34 |

EXAMPLE 7

Preparation of Cosmetic Cream Containing Crude Extract of *Astragalus Membranaceus*

The cosmetic cream was prepared by mixing components for making the basic cream with an effective amount of the astragaloside extract serving as an active ingredient of the cosmetic cream. The components included but not limited to various amounts of water, Isononyl Isononanoate, Butylene Glycol, Triethylhexanoin, Behenyl Alcohol, PEG-100 Hydrogenated Castor Oil, Glyceryl Stearate SE, Dimethicone, Macadamia Nut Oil, Jojoba Oil, Hydrogenated Lecithin, Methylparaben, DL-α-Tocopheryl Acetate, Butylparaben, Phenoxyethanol and Fragrance as listed in the Table 7.

TABLE 7

| Components | Cosmetic Cream containing H₂O insoluble fraction of extract from *Astragalus membranaceus* (in 100 g) | Basic Cream (in 100 g) |
|---|---|---|
| Water | to 100.00 g (or %) | to 100.00 g |
| Isononyl Isononanoate | 7.00 g | 7.00 g |
| Butylene Glycol | 5.00 g | 5.00 g |
| Triethylhexanoin | 3.00 g | 3.00 g |
| Behenyl Alcohol | 3.00 g | 3.00 g |
| PEG-100 Hydrogenated Castor Oil | 2.00 g | 2.00 g |
| Glyceryl Stearate SE | 1.00 g | 1.00 g |
| Dimethicone | 1.00 g | 1.00 g |
| Macadamia Nut Oil | 0.50 g | 0.50 g |
| Jojoba Oil | 0.50 g | 0.50 g |
| Hydrogenated Lecithin | 0.20 g | 0.20 g |
| Methylparaben | 0.15 g | 0.15 g |
| DL-α-Tocopheryl Acetate | 0.10 g | 0.10 g |
| Butylparaben | 0.10 g | 0.10 g |
| Phenoxyethanol | 0.10 g | 0.10 g |
| Fragrance | 0.07 g | 0.07 g |
| Water insoluble fraction | 0.02 g | — |

EXAMPLE 8

Clinical Trial

Test Subject

Twenty-five healthy volunteers (20 females and 5 males) aged from 35 years old and above were admitted to the clinical study with their consents. The test subjects were asked not to put any other cosmetic products on their faces during the whole period of study. The physical properties (skin pH, skin moisture content, transepidermal water loss, skin surface lipid, skin color and brightness, skin elasticity and skin roughness) of the skin were evaluated 30 minutes after the cleansing the subjects' faces to provide baseline measurements. Next, a suitable amount (e.g. size of a peanut) of the cosmetic cream comprising the extract of the invention was applied evenly on right side of the subject's face and equal amount of the basic cream was applied on the left side of the face to provide a comparison, and the same measurements were taken again 30 minutes after the creams were applied on the subject's face to provide short term effect data. All the tests were conducted at a room temperature ranged from about 24° C. to about 28° C., a relative humidity ranged from about 50% to about 60%. Each of the tests was carried out with each measurement taken from a test spot having a diameter of about 2 cm at three selected test areas (forehead, corner of the eye and upper cheek) on either side of the test subject's face.

Skin pH:

The measurements were made using Skin-pHMeter® PH 905 (Courage+Khazaka electronic) which had a probe equipped with sensor elements. The planar design of the probe head allowed direct measurement with skin contact.

Skin Color and Brightness (Ervthematic Index & Melanin Index):

The measurement was based on absorption/reflection of the light. The probe of the Mexameter® MX 18 (Courage+Khazaka electronic) emitted three specific light wavelengths. A receiver measured the light reflected by the skin. The positions of emitter and receiver ensured that only diffused and scattered light was measured. As the quantity of emitted light was defined, the quantity of light absorbed by the skin could be calculated. The melanin was measured by specific wavelengths chosen to correspond to different absorption rates by the pigments. The specific wavelengths corresponding to the spectral absorption peak of haemoglobin were also selected for the erythema measurement to avoid other color influences (e.g. bilirubin). The results for both parameters were shown as indices.

Skin Roughness:

The skin roughness was measured using Skin Visiometer SV (Courage+Khazaka Electronic, Köln, Germany) based on light transmission through a thin replica comprising blue-dyed two-component silicone of which the light absorption was known. With the thin replica inserted in a modified slide projector, light coming directly from a neon lamp penetrated the replica and was absorbed depending on the thickness of the silicone material. A video sensor charge couple device and a black and white (b/w) CMOS-camera with a resolution of 640×480 pixels measured the amount of locally transmitted light, and the light intensity was calculated according to Lambert and Beer's law of absorption.

The averaged measurements of the physical properties taken from 15 test subjects aged from 38 to 58 yrs old after 30 days of the treatment were listed in Table 8.

TABLE 8

| Item | pH value | Erythematic Index | Melanin Index | L value | Surface | Volume |
|---|---|---|---|---|---|---|
| left side | −8.00 | −4.25 | −22.95 | 0.68 | −2.79 | 3.29 |
| right side | −11.19 | 0.22 | −27.17 | −1.18 | −4.77 | −7.77 |

In accordance with the results shown in Table 8, a drop of averaged skin pH by 11.19% was detected on the right side of the test subject's face. So, the skin would be expected to maintain in a healthy condition with minimum growth of microorganisms due to slightly acidic environment achieved when the skin was treated with the cosmetic cream containing the water insoluble fraction of *Astragalus membranaceus* of the invention. In view of an averaged erythematic index of 0.22 detected, the right side of the test subject's face was more erythematic than the left side, suggesting that the right side of the face had a more efficient blood circulation. The melanin index measured on the right side of the face indicated that amount of melanin was reduced by 27.17%. Also, the skin brightness as measured in terms of L value was evaluated together with the erythrematic index and the melanin index. A drop of the L value by 1.18% suggested that the skin looked brighter after the cosmetic cream was applied for one month. Accordingly, the right side of the test subject's face would look as a whole more whitening and radiant than the left side.

The surface area of rufflings or folds was measured to determine the skin wrinkles on the test subject's face. As shown in Table 8, the average surface area decreased by 4.77% to reduce the skin wrinkles after the right side of the test subject's face was applied with the cosmetic cream for one month. The volume which measured the volume of the skin relative to the skin surface area was reduced by 7.77%. As a result, the depth and number of the wrinkles were reduced.

The compound may be administered to the subject in need of skin care as frequently as several times daily, or it may be administered less frequently, such as once a day, once a week, once every two weeks, once a month. The frequency of the dose will be readily apparent to the skilled artisan and will depend upon any number of factors, such as, but not limited to, the type and age of the subject, etc.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for enhancing collagen expression in skin cells, comprising topically administering a composition, including a water insoluble fraction of *Astragalus membranaceus* as the active ingredient, to a skin area in a subject in an amount effective for enhancing collagen expression, wherein the water insoluble fraction of *Astragalus membranaceus* is prepared by a process including:
   extracting *Astragalus membranaceus* with alcohol to obtain an alcohol extract;
   dispersing the alcohol extract, in dry form, in water and n-butanol at a volume ratio of 1:1; and
   collecting the water insoluble fraction.

2. The method according to claim 1, wherein the composition is a cosmetic cream.

3. The method of claim 1, wherein the composition further comprises at least one cosmetically acceptable carrier.

4. The method of claim 1, wherein the composition is administered to a healthy subject.

5. The method of claim 1, wherein the skin area is a facial skin area.

6. The method of claim 4, wherein the skin area is a facial skin area.

* * * * *